United States Patent [19]
Bonnefoy

[11] Patent Number: 4,840,495
[45] Date of Patent: Jun. 20, 1989

[54] METHOD AND APPARATUS FOR MEASURING THE THERMAL RESISTANCE OF AN ELEMENT SUCH AS LARGE SCALE INTEGRATED CIRCUIT ASSEMBLIES

[75] Inventor: Jean Bonnefoy, Crespieres, France
[73] Assignee: Bull S.A., Paris, France
[21] Appl. No.: 947,265
[22] Filed: Dec. 29, 1986
[30] Foreign Application Priority Data
Dec. 27, 1985 [FR] France ................... 85 19342

[51] Int. Cl.⁴ .................. G01N 27/18; G01R 31/26
[52] U.S. Cl. ................... 374/43; 324/73 PC
[58] Field of Search ........... 374/44, 45, 29, 43; 324/158 D, 158 F, 73 PC

[56] References Cited
U.S. PATENT DOCUMENTS

| | | | |
|---|---|---|---|
| 2,951,360 | 9/1960 | Sampson et al. | 374/44 |
| 3,266,290 | 8/1966 | Haacke | 374/44 |
| 3,279,239 | 10/1966 | Arends et al. | 374/44 |
| 3,662,587 | 5/1972 | Allen et al. | 374/44 |
| 3,745,460 | 7/1973 | Belzer et al. | 324/158 D X |
| 3,979,671 | 9/1976 | Meeker et al. | 324/158 F |
| 4,522,512 | 6/1985 | Atkins | 374/44 |

FOREIGN PATENT DOCUMENTS
1573300 5/1969 Fed. Rep. of Germany .
1080435 8/1967 United Kingdom .

OTHER PUBLICATIONS
Journal of Physics E. Scientific Instruments; vol. 17, No. 9; Sep. 1984 pp. 800-807—Corsan.
Soviet Journal of Quantum Electronics; vol. 14, No. 6; Jun. 1984, pp. 870-871—Arutyunyan et al.
Review of Scientific Instruments; vol. 54, No. 2; Feb. 1983, pp. 283-244; Sanders et al.

Primary Examiner—Daniel M. Yasich
Attorney, Agent, or Firm—Kerkam, Stowell, Kondracki & Clarke

[57] ABSTRACT

The measuring apparatus (10) according to the invention includes a hot source (14) and a cold source (18), each provided with a thermocouple (21, 22) and connected via a solid bar (17) of copper that is in contact with the hot source and is spaced apart from the cold source by a regulatable distance (19). The measuring method is based on calculating the thermal resistance $R = (T1 - T2)/Q$, where $T1 - T2$ and $Q$ are, respectively, the temperature difference and the thermal flux between the sources. R1 is calculated with the element (11), then R2 is calculated without the element (11). The difference $R1 - R2$ gives the thermal resistance of the element.

11 Claims, 1 Drawing Sheet

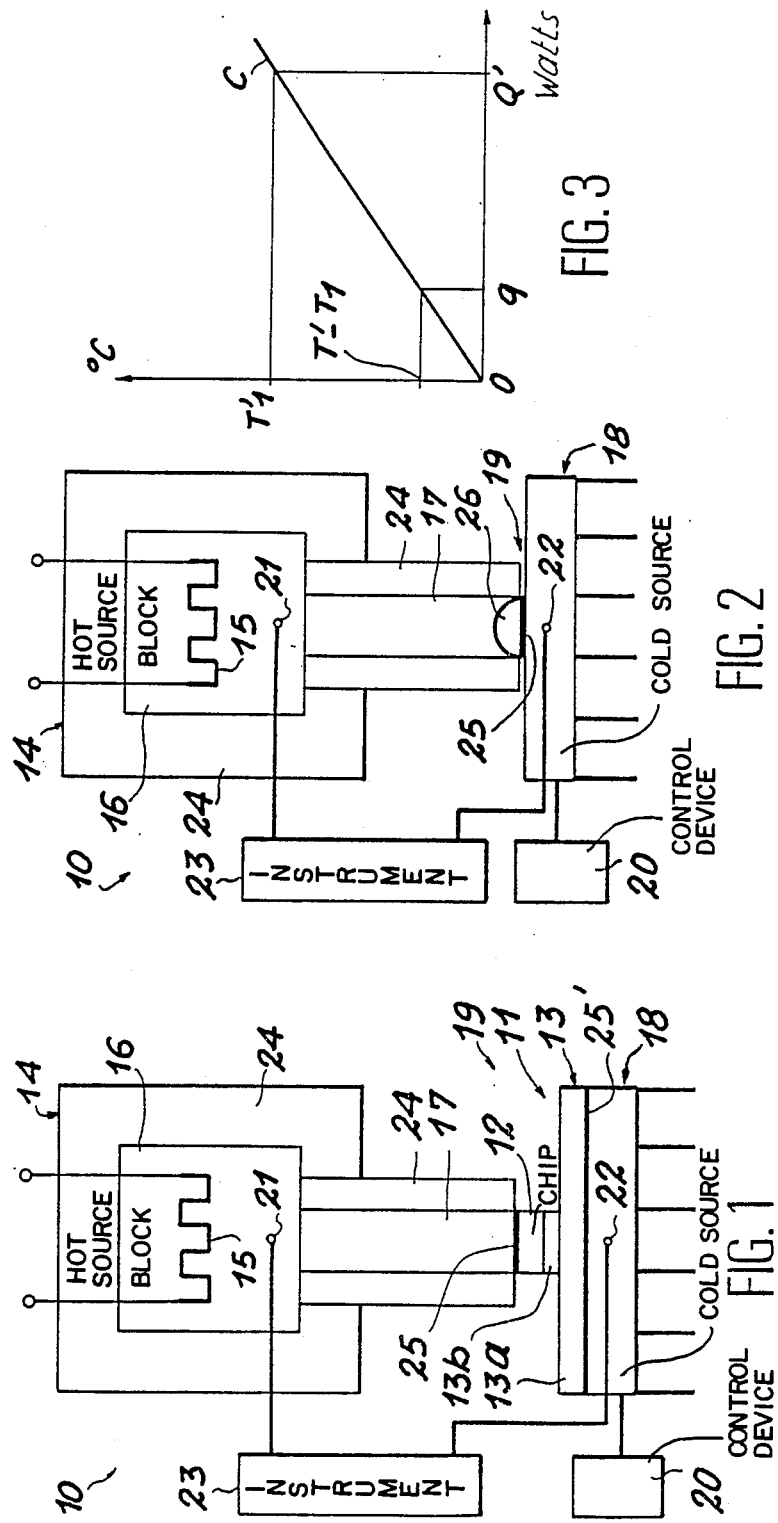

METHOD AND APPARATUS FOR MEASURING THE THERMAL RESISTANCE OF AN ELEMENT SUCH AS LARGE SCALE INTEGRATED CIRCUIT ASSEMBLIES

FIELD OF THE INVENTION

The present invention relates to a method and an apparatus for measuring the thermal resistance of an element and more particularly as applied to electronic equipment incorporating sources of heat such as integrated circuit assemblies, known as integrated circuits, chips or ICs.

BACKGROUND OF THE INVENTION

Integrated circuit assemblies generally include a chip, one face of which is provided with a layer of adhesive for affixing the integrated circuit or circuits. The chip may include an electrical mesh network of printed circuits and may cooperate with a cooling element, such as a dissipator glued onto the other face of the chip.

Increasingly large scale integration of integrated circuits on a silicon chip has the effect of increasing the density of the heat that has to be dissipated. Even if certain technologies for manufacturing transistors lessen their dissipation, the increase in the heat density to be dissipated remains, because of the very large scale integration that has by now been attained. To retain the advantage obtained by very large scale integration of integrated circuits, the chip assemblies, in order to be incorporated into a machine, must be adapted perfectly to all the characteristics of the chips. The solution that is adopted is often the best compromise between the mechanical, electrical and thermal characteristics of the elements involved. Since the mechanical and electrical characteristics are ordinarily known with precision, the best compromise cannot be obtained without precise measurement of the thermal characteristics.

Moreover, it is very interesting to measure the thermal resistance of all the elements comprising the heat dissipation route between a chip and the ambient air under actual operating conductions of a chip assembly. In these concrete instances, the measurements often diverge widely from the total resistance calculated on the basis of the thermal conductivities of the various materials used in the heat dissipation route. It is therefore very important to locate the source of these divergences in the heat dissipation route. For example, they may originate in the interfaces, in the porosity of a material that was made porous when it was applied, or from a drift in the thermal resistance of a material under the influence of the heat or some other external factor.

The Japanese patent published as No. 57-132046 describes a method and an apparatus for measuring the conductivity and thermal capacity of a specimen. This apparatus includes a copper plate that cooperates with a thermostat acting as a hot source, and a thin plate of acrylic. The two plates have two faces facing one another and intended for clamping the specimen, and each face is provided with a thermocouple. The method comprises, first, placing the specimen on the acrylic plate and waiting until it has uniformly assumed the ambient temperature. Then the copper plate is placed in the thermostat to make it assume a uniform temperature, and then is taken out of the thermostat and rapidly put into contact with the specimen. After 30 seconds, the temperatures at the thermocouples are read. Based on the temperature values ascertained and on the thickness of the specimen, in particular, the thermal conductivity of the specimen is determined, using charts prepared beforehand as a function of various parameters.

This method described in the above-identified Japanese Pat. No. 57-132046 is limited to measuring the thermal resistance of a specimen of a uniform thickness. Thus it cannot be used for measuring the thermal resistance of an assembly having a composite structure, the components of which have different surface areas and non-uniform thicknesses (in particular because they are not parallel). This is typical of an integrated circuit assembly. Furthermore, in the apparatus of the prior art the acrylic plate is a thermal insulator, which cannot act as a dissipator or as a cold source. As a result, the method of the prior art is based on the specific (or mass) heat that is transferred from the copper plate to the specimen per unit of time. In other words, there is no continuous circulation of a flow of heat between a hot source and a cold source. Thus it is not possible, with this method, to measure the thermal resistance of an integrated circuit assembly subject to actual operating conditions. This method is also poorly suited to specimens having a relatively large mass or strong thermal resistance. Moreover, the act of withdrawing the copper plate from a thermostat results in uncontrollable energy losses. The method of the prior art thus cannot handle wide divergences of temperature between the plates, such as those existing for example between the active components of the chip and its dissipator.

Finally, the reliance on charts presumes prior experience with known specimens subjected to particular, restrictive conditions. Also, calculation using intrapolation or extrapolation is involved. In conclusion, the method and apparatus of the prior art are unable to provide very precise and reliable measurement of the thermal resistance of any element of any kind, no matter whether its structure is simple or composite, and no matter what conditions it is subjected to.

Measuring the thermal resistance of a chip assembly subjected to actual operating conditions is accordingly done by a different method. The standard measuring method is performed only on the chip and its assembly. The chip comprises the hot source, and its assembly is connected to its cold source subjected to actual operating conditions. Then the thermal flux Q produced by the chip and transmitted to the cold source is measured, and hence the temperature T1 of the hot source and the temperature T2 of the cold source. The thermal resistance R between the chip and its cold source is calculated using the formula $R=(T1-T2)/Q$.

This method can provide only an overall value of the thermal resistance of the entire heat dissipation route between the chip and the ambient air. Accordingly, a defect along this route cannot be located with this method. Furthermore, this measurement proves to be increasingly inaccurate, the smaller the dimensions of the elements. Also, the precision of the measurement is affected by the imprecision of the measurement of the thermal flux Q effectively transmitted from the chip to the cold source. In fact, if the theoretical value of Q corresponds to the electric power furnished to the chip, in practice some of this power dissipates, by natural convection. As a consequence, the precise determination of Q in the above equation cannot be made unless the power losses q caused by natural convection are known.

OBJECT AND SUMMARY OF THE INVENTION

The invention proposes a method and an apparatus for precise measurement of the thermal resistance of an either simple or composite element. The invention thus makes it possible to measure all or part of the thermal route of a chip assembly and hence to locate the presence of a defect and to correct it efficaciously. The invention also provides the precise measurement of thermal resistances, because of the precise measurement of the temperatures T1, T2 and the thermal flux Q.

The method of measurement according to the invention of the thermal resistance of an element, comprising using a hot source and a cold source, measuring the temperature (T1) of the hot source, the temperature (T2) of the cold source and the thermal flux (Q) flowing from the hot source to the cold source, and calculating the thermal resistance (R) by applying the formula $R=(T1-T2)/Q$, is characterized in that it comprises connecting the element to the hot source via a solid bar that is a good thermal conductor and having a cross section at least approximately equal to the facing cross section of the element, calculating the thermal resistance (R1) representative of the bar and the element, removing the element and calculating the thermal resistance (R2) representative of the bar, and deducing the thermal resistance (R3) of the element by subtracting R2 from R1.

A measuring apparatus for performing the method according to the invention is characterized in that it includes a hot source and a cold source, each of them provided with a thermocouple and being connected via a solid bar of a material that is a good thermal conductor in contact with the hot source and spaced apart from the cold source by a regulatable distance.

The characteristics and advantages of the invention will become apparent from the ensuing detailed description of an exemplary embodiment, taken in conjunction with the drawings.

BRIEF DESCRIPTION OF THE DRAWINGS

FIG. 1 is a schematic view of a measuring apparatus according to the invention, illustrating one phase of the method according to the invention for measuring the thermal resistance of an element such as an integrated circuit assembly;

FIG. 2 is a view similar to that of FIG. 1, showing a variant embodiment of a measuring apparatus according to the invention, shown in a second phase of the method according to the invention; and FIG. 3 is a graph used for determining the calorific energy losses in the apparatus shown in FIGS. 1 and 2.

DESCRIPTION OF THE PREFERRED EMBODIMENT

FIG. 1 is a schematic illustration of a measuring apparatus 10 according to the invention for determining the thermal resistance of an element 11. The element 11 shown includes an integrated circuit or chip 12 its assembly 13, consisting simply of a substrate 13a provided with a layer of adhesive 13b for the affixing of the integrated circuit 12.

The measuring apparatus 10 includes a hot source 14 embodied for example by an electrical resistor 15 connected to a voltage source (not shown) and embedded in a block 16 of material that is a good thermal conductor, such as copper. The hot source 14 is in contact with one end of a solid bar 17 of material that is a good thermal conductor, such as copper. The other end of the bar 17 is placed facing a cold source 18, and spaced apart from it by a distance 19 that can be adjusted or regulated by means of a standard control device 20 of a type well known in the art. The cold source 18 shown is a dissipator, possibly ventilated. Two thermocouples 21, 22 are placed, respectively, in the mass of the block 16 of the hot source 14 and in the mass of the cold source 18, advantageously within the axis of the bar 17, so as to provide an instrument 23 with a signal representing the temperature T1 of the hot source 14 and a signal representing the temperature T2 of the cold source 18. The hot source 14 and the bar 17 are provided with a thermal insulation 24, to limit the power losses q by natural convection to a known value.

The method according to the invention for precise measurement of the thermal resistance of the element 11 is as follows. The element 11 is placed between the bar 17 and the cold source 18. Since the method of the invention is more particularly adapted for measuring a thermal resistance of an element subjected to actual operating conditions, the cold source 18 is thus supposed to be the dissipator with which the element 11 must normally be equipped, and it operates under actual operating conditions. Because of this, the chip 12 is in contact with the bar 17. For reasons of convenience which will become more apparent below, the bar 17 shown has a cross section identical to that of the element with which it is in contact, that is, that of the chip 12. The contact between the chip and the bar forms an interface 25, which will be described in due course. The hot source 14 is activated to furnish a given thermal power, and then there is a waiting period until a thermal equilibrium has been reached in the entire apparatus 10. In this state of equilibrium, the two temperatures T1 and T2 are stabilized and are read by the measuring instrument 23. Thus the difference $(T1-T2)$ that is part of the formula, $R=(T1-T2)/Q$ is measured precisely. What remains to be learned precisely is the value of the heat flux Q that effectively flows in the bar 17 and consequently in the element 11. The value of Q clearly corresponds to the power Q' furnished by the hot source 14, minus the power losses g due to natural convection. To determine the factor (Q'−q) precisely, the following method may be used. First, the heat source 14 is disconnected from the bar 17, and the reference curve representing the variations in the temperature T'1 at the thermocouple 21 is plotted as a function of the thermal power Q' furnished by the electric resistor 15. Thus a reference temperature T'1 is defined for each quantity of heat Q' that is capable of being emitted by the source 14 in its state of thermal equilibrium. Next, for the power Q' specifically furnished by the source 14 equipped with the bar 17, to make a measurement of thermal resistance according to the invention, the temperature T1 of the hot source is measured. The difference between the temperatures (T'1−T1) relative to the same power Q' corresponds to the losses q. For evaluating q, it is sufficient to consult the reference curve C to determine the power divergence corresponding to the difference (T'1−T1). From then on, the values of $(T1-T2)$ and of Q are known precisely, and they can furnish the value of the thermal resistance R1 of everything located between the sources 14 and 18, and including the bar 17 and the element 11.

Next, the measurement shown in FIG. 2 is done. The element 11 is removed from the apparatus 10, and the cold source 18 is put in contact with the bar 17. The interface 25 remains, but it connects the bar 17 with the dissipator 18 directly. After thermal equilibrium is reached, the temperature T'2 is read at the thermocouple 22, and the resistance $R2=(T1-T'2)/Q$, this time relative to the thermal resistance of the bar 17 and interface 25, is calculated. The thermal resistance R3 of the element 11 is then deduced by subtraction: $R2-R1$.

The interface 25 may simply be embodied by the direct contact of the bar 17 with the chip 12 of the element 11 in FIG. 1, or with the dissipator 18 in FIG. 2. However, the thermal resistance of any such direct contact interface is zero only if there is contact at every point of the interface, that is, if the facing surfaces are perfectly plane and parallel. Practical instances deviate to a varying degree from this state of perfection, especially as a function of the size of the facing surfaces. Because of imperfections, the interface not only has a thermal resistance that may no longer be negligible, but this resistance is also variable depending on the position of the contacting faces and on the forces involved. The interface must accordingly be given a constant value that can be known very precisely, so as to retain the precision of the thermal resistances measured and to make the measurements reproducible. To this end, the method according to the invention also comprises embodying the interface 25 as a gasket of viscous material that is a good thermal conductor, such as a silicone lubricant. Since the gasket 25 is common to two steps of the method shown in FIGS. 1 and 2, and since the value of R2 that is measured according to FIG. 2 includes the resistance of the gasket 25, the resistance of the gasket 25 does not have to be measured. However, it does prove to be necessary to provide a similar gasket to comprise the interface 25' between the element 11 and the dissipator 18. In that case, the thermal resistance of the gasket 25' is included in the value R3 and must be substracted out of the value R3 again in order to learn the precise thermal resistance of the element 11. One method of measuring the resistance of the gasket 25' may comprise replacing the element 11 with a solid piece of homogeneous material that is a good thermal conductor, such as copper, having a cross section that determines an interface 25' identical to the interface 25 of the element to be measured and having a predetermined thickness. The method according to the invention will result in a value R'3 representing the thermal resistance of the block of copper and of the gasket 25'. The thermal resistance of the block of copper is easily determined by calculation, taking into account the thermal resistivity of copper and the dimensions of the block. The difference between this value and R'3 gives the thermal resistance of the interface 25'.

Furthermore, it is very probable that an element 11 having a complicated structure will have lower and upper surfaces with defects in evenness or parallelism. In that case, placing the element 11 between the bar 17 and the dissipator 18 risks subjecting it to damaging strains, which can also falsify the measurements. This causes the interfaces to have nonuniform thicknesses, which is detrimental to the precision of measurement. The measuring apparatus 10 according to the invention can overcome this disadvantage, by giving the bar 17 the structure shown in FIG. 2 at the level of the surface 25. At that level, the corresponding face of the bar 17 is formed, by the plane face of an approximately hemispherical ball 26 pivotably housed in a suitable hollow in the bar. The resultant modification of the thermal resistance of the bar 17 has the advantage of being constant and of being included in the values R1, R2, such that the modification does not have to be measured.

The example described above referring to FIGS. 1 and 2 corresponds to the case where the cross sectional area or geometry, hereinafter referred to as "cross section", of the bar 17 is identical to the cross section of the facing surface of the element 11. It is now clear that this condition proves to be ideal, because the lines of flux of the heat are uniform in the bar up to the interface 25 that is included. However, this condition necessitates shaping the bar 17 as a function of the elements to be measured. When a great variety of cross sections of elements are to be measured, it will be preferable to make the cross section of the bar match the largest cross section of the elements that might be measured. For a smaller cross section, the lines of flux are confined to the level of the interface 25 and will perturb the measurements. Nevertheless a preliminary calibration may be made, for example by comparing the measurements with those obtained under ideal conditions where the cross section is the same between the bar 17 and the element 11.

Furthermore, a bar 17 having a slightly smaller cross section at the facing surface of the element 11 may be presumed not to perturb the measurements if the material making up the element at the level of the interface 25 is a relatively good thermal conductor. In that case, the temperature can be considered to be uniform throughout the material. This is the case, for example, with material of square cross section measured with a bar 17 having a cross section corresponding to the circle inscribed inside this square. However, if a perturbation is present, it could be taken into account in the calculations of the resistance of this material. Thus it can be said that as a general rule the cross section of the bar must be at least approximately equal to the facing surface of the specimen. The same applies for the interface 25'.

It is apparent from the above description that the method according to the invention applies equally well to any element, whether its structure is simple or composite. For an element of composite structure such as the element 11 shown in FIG. 1, the method of the invention has the advantage of determining the thermal resistance of each of its component parts. For example, by eliminating the chip 12 from the element 11 shown and then proceding to take measurements in accordance with the invention, the thermal resistance of the substrate 13 is determined, and by subtraction to obtain R3, the thermal resistance of the chip 12 is learned. Then, by eliminating the adhesive layer 13b from the substrate 13 and making measurements according to the invention, the thermal resistance of the substrate 13a is known, and by deduction the thermal resistance of the adhesive layer 13b is known.

What is claimed is:

1. In a method for determining the thermal resistance (R3) of an element (11), wherein a temperature (T1) of a hot source and a temperature (T2, T'2) of a cold source are measured, a thermal flux (Q) flowing from the hot source to the cold source is determined, and a thermal resistance (R1, R2) is calculated by applying the formula $R=(T-T2)/Q$, the improvement comprising:

connecting the element (11) to the hot source (14) via a serially connected solid bar (17) having a cross-section at least approximately equal to a facing cross-section of the element, said solid bar being a good thermal conductor;

measuring hot source temperature (T1) and cold source temperature (T2);

determining thermal flux (Q);

calculating a thermal resistance (R1) representative of the bar and the element by applying the formula $R1 = (T1 - T2)/Q$;

removing the element (11);

moving bar (17) into contact with cold source (18) via an interface (25);

measuring hot source temperature (T1) and cold source temperature (T'2);

determining thermal flux (Q);

calculating a thermal resistance (R2) representative of the bar by applying the formula $R2 = (T1 - T'2)/Q$; and calculating a thermal resistance (R3) of the element (11) by subtracting R2 from R1.

2. A method as defined by claim 1, including forming an interface (25, 25') between the element (11), the bar (17) and the cold source (18) as gaskets of viscous material that is a good thermal conductor.

3. A method as defined by claim 2, further including measuring the thermal resistance of the gasket (25) by replacing the element (11) with a block made of material having a known thermal resistivity, having a predetermined thickness and a cross section that reproduces the interface to be measured.

4. A method as defined by one of the claims 2 or 3, comprising determining the value of (Q) by plotting a reference curve representing the variations in temperature (T'1) at a given point (21) of a single hot source (14) as a function of the thermal power (Q') received by the hot source, then finding the temperature (T1) of the hot source at the given point from the measurement of temperature (T1) made in the method of determining the thermal resistance of element (11) having a given thermal power (Q'), deducing from the reference curve the thermal power losses (q) corresponding to the temperature difference (T'1 − T1), and determining the value of (Q) from the difference (Q' − q).

5. Apparatus for determining the thermal resistance of an element (11) comprising a hot source (14), means for measuring a temperature of said hot source comprising a first thermocouple (21) connected to the hot source, said first thermocouple further having means for indicating said temperature; a cold source, means for measuring a temperature of said cold source comprising a second thermocouple (22) connected to the cold source, said second thermocouple further having means for indicating said temperature, a solid bar (17) that is a good thermal conductor and having a cross section at least approximately equal to a facing cross section of the element (11) whose thermal resistance is to be, determined said solid bar being connected to said hot source, said solid bar further being disposed to connect the element to the hot source, and said bar being spaced from the cold source (18) at a sufficient distance whereby said element (11) whose thermal resistance is to be determined may be placed between said solid bar and said cold source.

6. Apparatus as set forth in claim 5 further including means for adjusting the distance said cold source (18) is spaced from the bar 7. Apparatus as set forth in claim 5 further comprising interface elements (25, 25') between the element (11), the bar (17) and the cold source (18), when said element (11) is placed between said bar (17) and said cold source (18), wherein said interface elements are gaskets of viscous material that is a good thermal conductor.

8. An apparatus as set forth in claim 5, wherein the bar (17) includes, at the level of the spacing distance (19), a joint comprising an element having a planar face said element being pivotably housed in a hollow in the bar, and wherein said planar surface is arranged facing the cold source.

9. An apparatus as defined by claims 5, 6, 7 or 8 wherein the hot source (14) comprises an electrical resistor (15) embedded in a block (16) of a good thermal conductor.

10. An apparatus as defined by claim 9 wherein the block (16) and the bar (17) are disposed in a thermal insulation (24).

11. A method for determining a thermal resistance (R3) of an element (11) comprising:

(a) connecting the element to a hot source (14) and a cold source (18), said element being connected to said hot source by a serially connected solid bar (17) that is a good thermal conductor said bar having a cross-section at least approximately equal to a facing cross-section of said element (b) measuring a temperature (T1) of said hot source;

(c) measuring a temperature (T2) of said cold source;

(d) determining a thermal flux (Q) flowing from the hot source to the cold source;

(e) calculating a total thermal resistance (R1) representative of said element (11) and said bar (17) by applying the formula $R1 = (T1 - T2)/Q$;

(f) removing said element (11) from between said bar (17) and said cold source (18);

(g) connecting the bar and the cold source via an interface (25);

(h) measuring a temperature (T1) of the hot source;

(i) measuring a temperature (T'2) of the cold source;

(j) determining a thermal flux (Q) flowing from the hot source to the cold source;

(k) calculating the thermal resistance (R2) representative of the bar by applying the formula $R2 = (T1 - T'2)/Q$; and (l) calculating a thermal resistance (R3) of the element (11) alone by subtracting the thermal resistance (R2) representative of the bar, from the thermal resistance (R1) representative of the element (11) plus the bar (17).

* * * * *

UNITED STATES PATENT AND TRADEMARK OFFICE
CERTIFICATE OF CORRECTION

PATENT NO. : 4,840,495
DATED : June 20, 1989
INVENTOR(S) : BONNEFOY

It is certified that error appears in the above-identified patent and that said Letters Patent is hereby corrected as shown below:

In Col. 6, line 64, (Claim 1), "$R=(T-T2)/Q$" should be --$R=(T1-T2)/Q$--.

In Col. 7, line 8, (Claim 1), "$R2=(T1-T2)/Q$" should be --$R2=(T1-T'2)/Q$--.

In Col. 8, line 34, (Claim 11), after "element" insert --(11);--.

In Col. 8, line 6, (Claim 6), after "bar" insert --(17).--.

In Col. 8, 53, (Claim 11), "$R2=(T1-T2)/Q$" should be --$R2=(T1-T'2)/Q$--.

Signed and Sealed this

Seventeenth Day of April, 1990

*Attest:*

HARRY F. MANBECK, JR.

*Attesting Officer*     *Commissioner of Patents and Trademarks*